United States Patent
Perrin et al.

(10) Patent No.: US 11,224,338 B2
(45) Date of Patent: Jan. 18, 2022

(54) METHOD AND SYSTEM FOR MEASURING REFRACTION, METHOD FOR THE OPTICAL DESIGN OF AN OPHTHALMIC LENS, AND PAIR OF GLASSES COMPRISING SUCH AN OPHTHALMIC LENS

(71) Applicant: ESSILOR INTERNATIONAL, Charenton-le-Pont (FR)

(72) Inventors: Jean-Luc Perrin, Charenton-le-Pont (FR); Guilhem Escalier, Charenton-le-Pont (FR); Isabelle Poulain, Charenton-le-Pont (FR); Benjamin Rousseau, Charenton-le-Pont (FR); Cécile Petignaud, Charenton-le-Pont (FR); Gildas Marin, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 312 days.

(21) Appl. No.: 16/467,306

(22) PCT Filed: Oct. 27, 2017

(86) PCT No.: PCT/FR2017/052971
§ 371 (c)(1),
(2) Date: Jun. 6, 2019

(87) PCT Pub. No.: WO2018/104602
PCT Pub. Date: Jun. 14, 2018

(65) Prior Publication Data
US 2020/0069172 A1    Mar. 5, 2020

(30) Foreign Application Priority Data

Dec. 7, 2016  (FR) ...................................... 1662085

(51) Int. Cl.
*A61B 3/028*  (2006.01)
*A61B 3/00*  (2006.01)
*A61B 3/103*  (2006.01)

(52) U.S. Cl.
CPC ............ *A61B 3/028* (2013.01); *A61B 3/0075* (2013.01); *A61B 3/0083* (2013.01); *A61B 3/103* (2013.01)

(58) Field of Classification Search
CPC ..... A61B 3/028; A61B 3/0075; A61B 3/0083; A61B 3/103
(Continued)

(56) References Cited

U.S. PATENT DOCUMENTS 8,360,580 B2   1/2013  Chauveau
9,521,951 B2   12/2016 Baranton et al.
(Continued)

FOREIGN PATENT DOCUMENTS

CN   104010561 A   8/2014
CN   104412149 A   3/2015
(Continued)

OTHER PUBLICATIONS

International Search Report, dated Feb. 16, 2018, from corresponding PCT application No. PCT/FR2017/052971.
(Continued)

*Primary Examiner* — Mohammed A Hasan
(74) *Attorney, Agent, or Firm* — Nixon & Vanderhye

(57) ABSTRACT

Disclosed is a method for measuring the refraction of an individual by a refraction measuring appliance, including: an initial step of determining at least one initial value of a visuo-postural parameter of the individual; a step of processing the initial value in order to deduce at least one initial value of a regulating parameter of the refraction measuring appliance, the regulating parameter being associated with
(Continued)

the visuo-postural parameter; a step of regulating the refraction measuring appliance according to the initial value of the regulating parameter; and a step of measuring the refraction of the individual by the measuring appliance regulated in this way. Also disclosed is a method for the optical design of an ophthalmic lens, and to a pair of glasses including such a lens.

12 Claims, 7 Drawing Sheets

(58) Field of Classification Search
USPC .......................................................... 351/222
See application file for complete search history.

(56) References Cited

U.S. PATENT DOCUMENTS

| | | | |
|---|---|---|---|
| 9,545,202 B2 | 1/2017 | Divo et al. | |
| 9,955,864 B2 | 5/2018 | Rousseau et al. | |
| 10,278,573 B2 | 5/2019 | Boutinon et al. | |
| 2005/0007551 A1* | 1/2005 | Wakil | A61B 3/1015 351/205 |
| 2005/0105049 A1* | 5/2005 | Maeda | A61B 3/0075 351/208 |
| 2010/0128220 A1 | 5/2010 | Chauveau | |
| 2013/0100410 A1* | 4/2013 | Liang | A61B 3/1015 351/223 |
| 2015/0146168 A1* | 5/2015 | Divo | A61B 3/0008 351/204 |
| 2015/0374224 A1* | 12/2015 | Baranton | A61B 3/085 351/206 |
| 2017/0027435 A1 | 2/2017 | Boutinon et al. | |

FOREIGN PATENT DOCUMENTS

| | | |
|---|---|---|
| FR | 2914173 A1 | 10/2008 |
| FR | 2984716 A1 | 6/2013 |
| FR | 2992843 A1 | 1/2014 |
| JP | 2016-028760 A | 3/2016 |
| WO | 2013/093363 A1 | 6/2013 |
| WO | 2015/092244 A1 | 6/2015 |
| WO | 2015/101737 A1 | 7/2015 |
| WO | 2015/155456 A1 | 10/2015 |
| WO | 2015/155458 A1 | 10/2015 |

OTHER PUBLICATIONS

French Search Report, dated Jul. 25, 2017, from corresponding FR application No. 1662085.
Office Action issued in Chinese Patent Application No. 201780075608.2 dated Apr. 27, 2021.

* cited by examiner

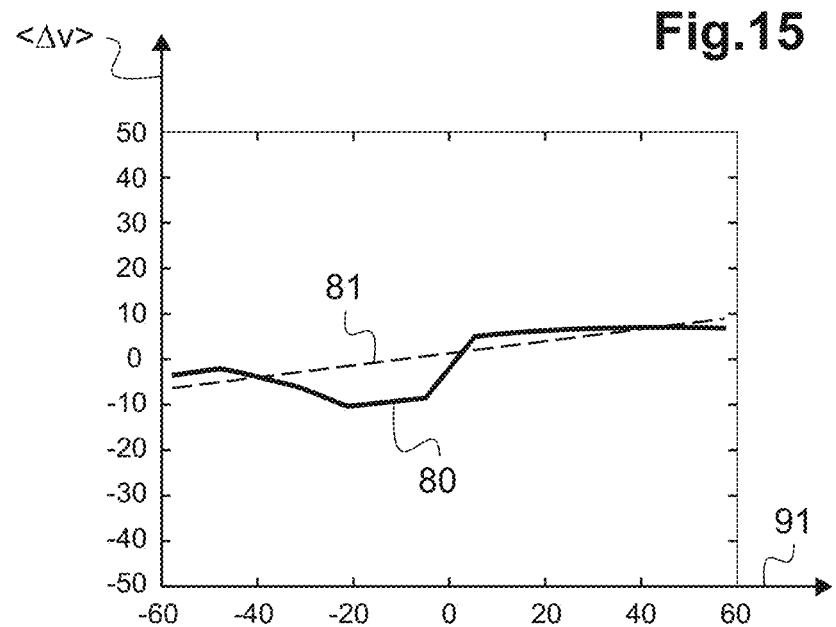
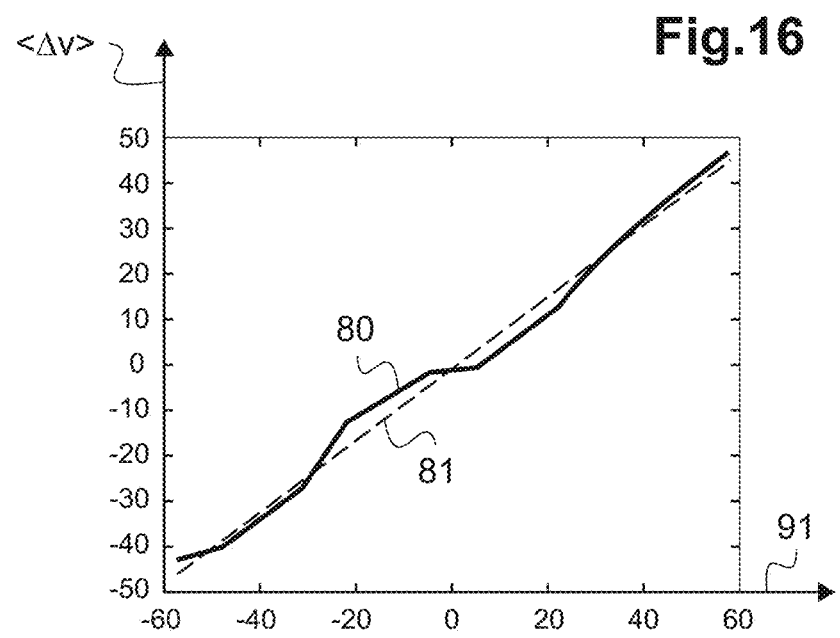

METHOD AND SYSTEM FOR MEASURING REFRACTION, METHOD FOR THE OPTICAL DESIGN OF AN OPHTHALMIC LENS, AND PAIR OF GLASSES COMPRISING SUCH AN OPHTHALMIC LENS

TECHNICAL FIELD OF THE INVENTION

The present invention generally relates to the field of optometry and of the optical design of ophthalmic lenses.

It more particularly relates to a method for measuring the refraction of an individual.

It also relates to a system suitable for implementing this method and to a computer program usable in said system and intended to automate one or more steps of said measuring method.

It moreover relates to a method for optical design of an ophthalmic lens and to a method for selecting a spectacle frame on the basis of the refraction measurement obtained with said measuring method.

It lastly relates to a pair of spectacles comprising such an ophthalmic lens or indeed such a frame.

TECHNOLOGICAL BACKGROUND

Conventionally, measurements of the refraction of an individual are carried out with a measuring apparatus (refractometer or trial frame for example) under measurement conditions that differ, sometimes by quite a lot, from those under which the individual will wear his item of vision-correcting equipment, equipped with one or two ophthalmic lenses intended to correct this refraction.

In other words, the refraction measurements carried out on the individual are carried out by means of a standard measuring apparatus, for which the adjustment parameters are set a priori, without taking into account potential visuo-postural parameters of the individual.

Throughout this patent application, the expression "visuo-postural parameter" will be understood to mean a parameter regarding the posture of the individual in a vision situation or during a visual activity. The posture of the individual will be understood in a broad sense to comprise either a datum relating to the positioning (position/orientation) of his head and/or of his eye or eyes. In an even broader sense, the posture of the individual will possibly also be understood to comprise a datum relating to the positioning of the trunk of the individual.

For example, during a measurement of visual acuity in near vision, the distance generally used to perform the appropriate visual test is set to a standardized value of 33 or 40 centimeters. However, it is possible for this standardized distance to not correspond to the actual reading distance of the individual when the latter is in a natural reading posture. It therefore follows that the refraction measurement is biased and that the vision-correcting equipment prescribed depending on this visual acuity measurement will prove to be not or not very suitable for restoring a sufficient acuity.

In the same way, the measurement of the refraction of an individual is conventionally carried out without vision-correcting equipment (for example the last prescribed item of equipment) and almost always without the frame that the individual could choose for his new prescription. However, wearing a frame, with or without ophthalmic lenses, has an impact on the posture of the individual under worn conditions and also on the way in which the latter carries out visual acuity tests.

Thus, conventional refraction measurements are not carried out under conditions in which the posture of the individual is natural and unconstrained, nor with the frame that he would like to wear.

Therefore, the refraction measurements carried out using prior-art measuring methods are not very personalized and may prove to be approximative or, at the very least, unsuitable for the prescription of a new item of vision-correcting equipment.

SUBJECT OF THE INVENTION

In order to remedy the aforementioned drawback of the prior art, the present invention proposes a method for measuring the refraction of an individual that allows the posture and visual behavior of the individual under worn conditions to be better taken into account.

More particularly, according to the invention a method for measuring the refraction of an individual by means of a refraction-measuring apparatus is provided, this method comprising:

a) an initial step of determining, with or without initial vision-correcting equipment, at least one initial value of a visuo-postural parameter of said individual;

b) a step of processing said initial value of the visuo-postural parameter determined in step a) in order to deduce at least one initial value of an adjustment parameter of said refraction-measuring apparatus, said adjustment parameter being associated with said visuo-postural parameter;

c) a step of adjusting said refraction-measuring apparatus depending on said initial value of the adjustment parameter, i.e. the value deduced in step b); and d) a step of measuring the refraction of said individual by means of said refraction-measuring apparatus adjusted in step c).

Thus, by virtue of the use of one or more adjustment parameters, respectively deduced from one or more visuo-postural parameters of the individual, to adjust beforehand the measuring apparatus intended to take the measurement, it is possible to carry out this measurement under conditions for which the individual in visual activity is in the most natural possible posture and adopts a habitual visual behavior.

By virtue of the prior adjustment of the measuring apparatus with the one or more initial values of these adjustment parameters, the measurement of the refraction therefore takes into account a priori visuo-postural parameters of the individual and becomes a personalized measurement of the refraction of the individual. This measurement is also more representative of the actual worn conditions that the individual will possibly experience with a future item of vision-correcting equipment prescribed in correspondence with this personalized refraction measurement.

According to one particularly advantageous embodiment of the invention, the refraction-measuring method furthermore comprises:

e) a step of equipping the individual with an item of vision-correcting test equipment suitable for correcting the refraction measured in step d);

f) an additional step of determining, with said test equipment, at least one additional value of said visuo-postural parameter of said individual;

g) an additional step of processing said additional value of the visuo-postural parameter determined in step f) in order to deduce at least one following value of said adjustment parameter associated with said visuo-postural parameter;

and, next, steps c) and d) of the method are repeated with said following value of the adjustment parameter in order to measure a new value of the refraction of the individual by means of said refraction-measuring apparatus adjusted depending on this following value of the adjustment parameter.

According to another particularly advantageous embodiment of the invention, the refraction-measuring method furthermore comprises:

e) a step of equipping the individual with an item of vision-correcting test equipment suitable for correcting the refraction measured in step d);

f) an additional step of determining, with said test equipment, at least one additional value of said visuo-postural parameter of said individual;

g) an additional step of processing said additional value of the visuo-postural parameter determined in step f) in order to deduce at least one following value of said adjustment parameter associated with said visuo-postural parameter;

h) a step of comparing said initial and following values of said adjustment parameter, and:

when the comparison of step h) indicates that said initial and following values of said adjustment parameter differ by more than a predetermined difference threshold, steps c) and d) of the method are repeated with said following value of the adjustment parameter in order to measure a new value of the refraction of the individual by means of said refraction-measuring apparatus adjusted depending on this following value of the adjustment parameter and said new value of the refraction and the value of the refraction measured in step d) are recorded; and when the comparison of step h) indicates that said initial and additional values differ by less than said predetermined difference threshold, said additional value determined in step f) and said refraction measured in step d) are recorded.

The methods according to these two embodiments make it possible to converge towards a personalized measurement of the refraction of the individual that is even more precise and more representative of the worn conditions of the individual.

The following are other nonlimiting and advantageous features of the measuring method according to the invention, which may be implemented individually or in any technically possible combination:

said visuo-postural parameter of the individual determined in step a) comprises one of the following parameters:
  a natural posture of the head of the individual;
  a visual behavior parameter in natural posture;
  an eye/head coefficient;
  a reading distance in near vision;
  an offset value of a point of fixation with respect to the median plane of the head of the individual;
  an angle of lowering of the gaze;
  a parameter of convergence of the two eyes in near vision;
  a gaze direction.

in step a), said individual is equipped with a spectacle frame, optionally provided with ophthalmic lenses; and, in step c), said measuring apparatus is also adjusted depending on at least one complementary adjustment parameter, said complementary adjustment parameter comprising:
  a lens-eye distance;
  a pantoscopic angle of said frame;
  a wrap parameter of said frame;
  a parameter of centralness of the ophthalmic lenses in said spectacle frame.

said visuo-postural parameter of the individual being identical to said adjustment parameter of the refraction-measuring apparatus adjusted in step c), said processing of step b) consists in making said initial value of the adjustment parameter equal to said initial value of the visuo-postural parameter.

The invention also proposes an optical design method for designing an ophthalmic lens intended for an individual, comprising the following steps:

i) determining a value of the refraction of the individual by virtue of the implementation of the measuring method according to the invention; and ii) determining an optical profile of said ophthalmic lens depending on said measured refraction value.

By virtue of the implementation of the measuring method according to the invention, the measurement of the refraction of the individual is more precise and the optical design of the ophthalmic lens is better suited to the vision correction of the individual.

The optical design method therefore allows a better personalization of the vision-correcting equipment intended for the individual.

In addition, one particularly advantageous application of this optical design method is to the design of an ophthalmic lens intended to improve the visual comfort of an individual.

Moreover, the invention also proposes a method for assisting in the selection of a spectacle frame on the basis of the results of the refraction measurement obtained with the measuring method according to the invention.

The invention thus also proposes a pair of spectacles comprising at least one ophthalmic lens designed using said optical design method and/or a spectacle frame selected using said selection-assisting method.

The invention lastly proposes a system for implementing the method for measuring the refraction of an individual according to the invention, said system comprising:
  a vision-testing device suitable for evaluating said visuo-postural parameter of the individual;
  computing means suitable for deducing a value of an adjustment parameter from a value of the visuo-postural parameter of the individual evaluated by the vision-testing device; and
  a refraction-measuring apparatus suitable for being adjusted depending on said adjustment-parameter value deduced by the computing means and for measuring the refraction of the individual.

Another invention relates to a computer program suitable for performing the computations in step b) of the method for measuring the refraction of an individual when it is loaded into and executed by said computing means of the aforementioned system.

DETAILED DESCRIPTION OF ONE EXAMPLE EMBODIMENT

The description which follows with reference to the appended drawings, which are given by way of nonlimiting examples, will make it easy to understand what the invention consists of and how it may be achieved.

In the appended drawings:

FIGS. 15 and 16 are curves illustrating the computation of parameters of the visual behavior of the individual when he is looking at the target of the protocol of FIG. 5.

By way of preamble, it will be noted that identical or similar elements of the various embodiments shown in the various figures are referenced with the same reference signs and are not described each time.

It will also be noted that in the disclosure which follows, the terms "top" (or "upper") and "bottom" (or "lower") will be used in relation to the individual, top designating the side turned towards the head of the individual and bottom designating the side turned towards the feet of the individual.

Likewise, the term "front" will designate the side turned towards the individual, the term "rear" designating the side opposite to the front side.

In the rest of the present patent application, by measurement of the refraction of an individual what is meant is the determination of the optical properties of one and/or both of the two eyes of the individual by an ophthalmologist, an optometrist or indeed an optician.

The measured optical properties commonly comprise (positive or negative) spherical power, astigmatism (cylindrical power and axis) and more particularly astigmatism in near vision, exophoria or esophoria (prismatic power), and accommodation power (spherical power addition in near vision). Other optical properties may further include sensitivity to contrast, sensitivity to haze, visual acuity, optical aberrations of the eye of higher order, stereoscopic acuity, color vision or indeed the extent of the visual field.

Figure 1:
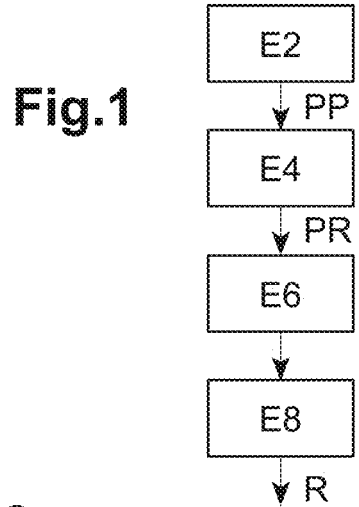
FIG. 1 shows a schematic chart of a first embodiment of the refraction-measuring method proposed by the invention.

FIG. 1 schematically shows the main steps of a first example embodiment of a refraction-measuring method according to the invention.

This method starts with a step E2 of determining, using a vision-testing device, a value of a visuo-postural parameter PP of the individual the refraction of whom it is desired to measure.

In the example described here, the individual is then wearing no vision-correcting equipment.

Provision could however as a variant be made for the individual to wear an item of vision-correcting equipment, for example vision-correcting spectacles (spectacles formed from a frame bearing at least one ophthalmic lens) produced on the basis of a prior prescription, or a trial frame (the correction made by this trial frame possibly being selected using conventional methods that are less precise than the refraction-measuring method described here).

According to another variant, the individual could then be wearing an empty frame (i.e. one devoid of ophthalmic lenses).

The visuo-postural parameter PP in question is for example a reading distance in near vision, an angle of lowering of the gaze (in particular in near vision), a parameter of convergence of the two eyes (in particular in near vision), or a gaze direction (for example in near vision).

An example of one possible implementation of the aforementioned step E2 using one particular vision-testing device is described below, with reference to FIGS. 4 to 16. In the context of this example, the determined visuo-postural parameter PP is the gaze direction (here in near vision) or the near-vision behavior (NVB) posture centroid described below (datum on the basis of which it is possible to determine the direction of the gaze and/or reading distance as indicated below).

In the case where the individual is wearing a frame (whether it be a question of a frame equipped with ophthalmic lenses or not as explained above), it is also possible to measure at this juncture at least one geometrico-morphological parameter characteristic of the way in which this frame is worn by the individual (i.e. associated with the individual-frame pair), such as for example a lens-eye distance, a pantoscopic angle of said frame, a wrap parameter of said frame or a parameter of centralness of the ophthalmic lenses in said spectacle frame. A method such as described in document WO 2015/101737 may be used to do so.

Once the value of the visuo-postural parameter PP has been determined, the method continues in step E4 with processing of this PP value, in order to deduce therefrom a value of an adjustment parameter PR associated with the aforementioned visuo-postural parameter.

This processing may in practice be carried out by a dedicated processing apparatus. Such a processing apparatus may comprise a module for receiving the value of the visuo-postural parameter PP determined in step E2 and a module for controlling a refraction-measuring apparatus, as explained below. The aforementioned receiving module is for example designed to enter into communication and to exchange data (in particular the value PP) with the apparatus used to determine the value of the visuo-postural parameter PP in step E2.

As a variant, the value of the visuo-postural parameter PP may be processed by the apparatus for determining this parameter (apparatus used to implement step E2, for example an apparatus such as described below with reference to FIGS. 4 to 16).

According to yet another variant, the value of the visuo-postural parameter PP may be processed by the refraction-measuring apparatus used to implement steps E6 and E8, which steps are described below.

In the example described here, this processing of step E4 consists for example in converting a value of lowering of the gaze in near vision into an angle of orientation of the refraction-measuring apparatus.

In certain embodiments, the visuo-postural parameter of the individual is identical to the adjustment parameter of the refraction-measuring apparatus; the aforementioned processing may then consist in making said value PR of the adjustment parameter equal to said value PP of the visuo-postural parameter.

The processing may furthermore include a conversion of the measured value PP of the visuo-postural parameter into a generally observed value corresponding to the same visuo-postural parameter, this conversion being carried out according to a predefined rule. Specifically, it has been observed that there generally is a predictable discrepancy between the value PP of the visuo-postural parameter measured during a visual test and the actual value of the same visuo-postural parameter in commonplace situations (i.e. when not being tested).

The method continues in step E6 with adjustment of the refraction-measuring apparatus (already mentioned above) depending on the value of the adjustment parameter PR obtained by the processing of step E4.

The refraction-measuring apparatus is for example a phoropter such as described in document WO 2015/155458 or even in document WO 2015/092244. The aforementioned control module may thus, after conversion of a value of lowering of the gaze into an angle of orientation, control an actuator of the aforementioned phoropter in order to orient the orientable holder of the phoropter depending on this angle of orientation.

If step E4 is carried out by a dedicated processing apparatus, the value of the adjustment parameter PR may be transmitted (for example by means of a communication system) from this processing apparatus to the refraction-measuring apparatus. As a variant, the practitioner may adjust the refraction-measuring apparatus depending on indications relating to the value of the adjustment parameter PR, which indications are given by the dedicated processing apparatus (for example by display of the value of the adjustment parameter PR on a screen of the dedicated processing apparatus).

It is then possible to implement a step E8 of measuring the refraction of the individual by means of the refraction-measuring apparatus, here the aforementioned phoropter.

The refraction measurement is thus carried out under postural conditions that are natural for the individual so that the item of vision-correcting equipment produced subsequently on the basis of the results of this refraction measurement will be particularly well suited to the individual.

In the case where at least one geometrico-morphological parameter characteristic of the way in which a frame is worn by the individual was measured in step E2, the refraction-measuring apparatus may furthermore be adjusted in conformity with one of these parameters. Specifically, it is for example possible to adjust the phoropter or the trial frame so that the position of the trial lenses corresponds to the envisioned position of the lenses (such as defined by the frame worn in step E2).

Provision may optionally furthermore be made, after implementation of the aforementioned refraction-measuring step and when the refraction-measuring apparatus cannot be precisely adjusted to the value PR of the adjustment parameter determined in step E4, for a final correcting step intended to correct the value of the refraction thus measured in order to take into account a disparity between the value PR of the adjustment parameter determined in step E4 and the value to which it was possible to adjust the refraction-measuring apparatus in step E6.

The refraction measurement of step E8 allows a refraction value R (or correction value) associated with the individual to be obtained. In practice, at least one refraction value R is measured naturally for each eye of the individual. As already indicated, such a refraction value R is for example a spherical-power value, a cylindrical-power value or a cylindrical-correction axis.

Specifically, the refraction value of the individual measured in step E8 is then used, in the context of an optical design method for designing an ophthalmic lens intended for this individual, to determine the optical profile of this ophthalmic lens (so that this optical profile allows the desired correction to be obtained, which correction is in particular defined by the measured refraction value, while optionally furthermore taking into account the aforementioned geometrico-morphological parameters).

Figure 2:
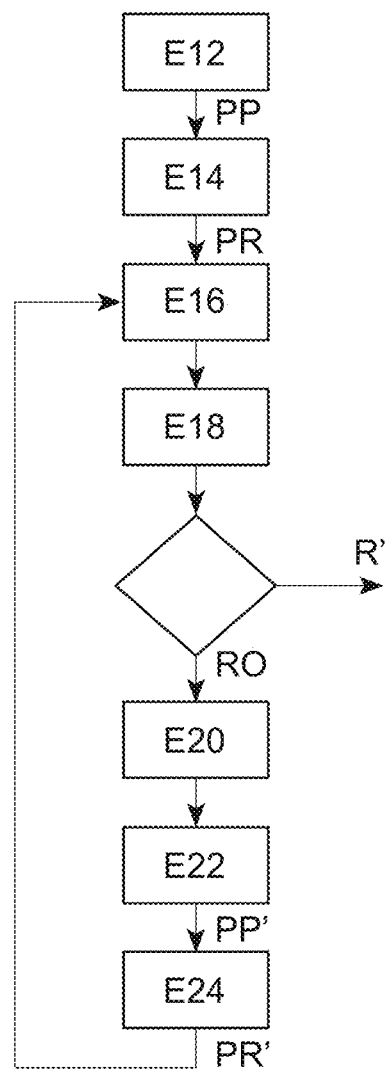
FIG. 2 shows a schematic chart of a second embodiment of the refraction-measuring method proposed by the invention.

FIG. 2 schematically shows the main steps of a second example embodiment of a refraction-measuring method according to the invention.

As will be clear from what is indicated below, steps E12 to E18 correspond to steps E2 to E8 described above with reference to FIG. 1 and they will therefore not be described in detail again. The observations and variants mentioned in the context of the description of steps E2 to E8 may be applied to steps E12 to E18, which will now be described.

The method of FIG. 2 starts with an initial step E12 of determining at least one initial value PP of a visuo-postural parameter of the individual for whom it is desired to measure the refraction, this step being carried out without initial vision-correcting equipment.

The method then comprises a step E14 of processing said initial value of the visuo-postural parameter PP in order to deduce at least one initial value of an adjustment parameter PR associated with said visuo-postural parameter.

The method then continues with a step E16 of adjusting a refraction-measuring apparatus depending on said initial value PR of the adjustment parameter.

The method then comprises a step E18 of measuring the refraction of the individual by means of said refraction-measuring apparatus such as it was adjusted in step E16. Thus an initial refraction value RO of the individual is obtained.

After the first passage through step E18, the method continues in step E20, in which the individual is equipped by means of an item of vision-correcting test equipment suitable for correcting the refraction RO measured in step E18. (The case of the second passage through step E18 is described below).

Such an item of vision-correcting test equipment is for example a pair of vision-compensating spectacles such as described in document WO 2015/155456. In the case where a control module is used as described above with reference to FIG. 1, the control module for example transmits instructions to such vision-compensating spectacles in order that the latter generate a correction corresponding to the refraction measured in step E18.

Provision is then made, in the example described here, for an additional step E22 of determining at least one additional value PP' of the aforementioned visuo-postural parameter, while the individual is equipped with the item of test equipment. The vision-testing device already mentioned as being used to implement step E2, and described below with reference to FIGS. 4 to 16, is for example used to do so.

The method may thus continue with an additional step E24 of processing said additional value PP' of the visuo-postural parameter in order to deduce at least one following value PR' of the adjustment parameter associated with said visuo-postural parameter. This processing is of the same type as the processing of step E4 described above and will therefore not be described in detail here.

As may be seen in FIG. 2, the method then loops to step E16, while however using the following value PR' of the adjustment parameter instead of the initial value PR.

The refraction-measuring apparatus is thus adjusted with the following value PR' of the adjustment parameter and may thus be used to measure a new value R' of the refraction of the individual.

After this second refraction measurement, the method may be terminated and the new value R' (obtained in the second passage through step E18) may then be used as result of the measuring method.

As already indicated, the refraction value (here R') of the individual obtained by virtue of the measuring method may then be used, in the context of an optical design method for designing an ophthalmic lens intended for this individual, to determine the optical profile of this ophthalmic lens (so that this optical profile allows the desired correction to be obtained, which correction is in particular defined by the measured refraction value R').

An ophthalmic lens that is particularly suited to the individual is thus obtained since the refraction measurement used to design the ophthalmic lens was not only carried out with the individual in a posture that was natural for him, but furthermore in a situation in which the individual was wearing an item of vision-correcting equipment, such as will be the case when he uses the ophthalmic lens.

Figure 3:
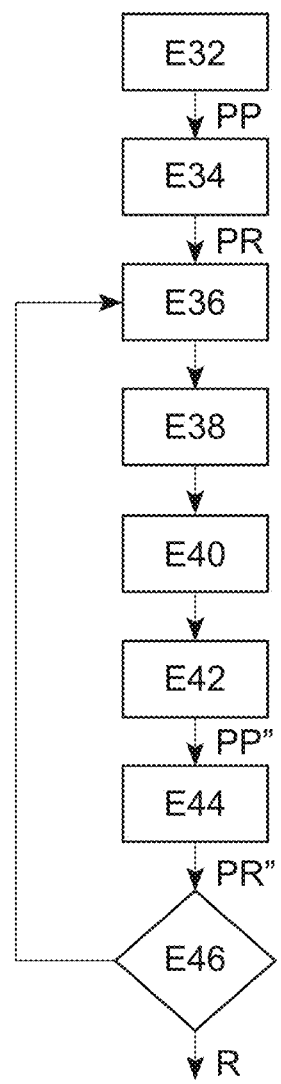
FIG. 3 shows a schematic chart of a third embodiment of the refraction-measuring method proposed by the invention.

FIG. 3 schematically shows the main steps of a third example embodiment of a refraction-measuring method according to the invention.

As will be clear from what is indicated below, steps E32 to E38 correspond to steps E2 to E8 described above with reference to FIG. 1 and they will therefore not be described in detail again. The observations and variants mentioned in the context of the description of steps E2 to E8 may be applied to steps E32 to E38, which will now be described.

The method of FIG. 3 starts with an initial step E32 of determining at least one initial value PP of a visuo-postural parameter of the individual for whom it is desired to measure the refraction, this step being carried out without initial vision-correcting equipment.

The method then comprises a step E34 of processing said initial value PP of the visuo-postural parameter in order to deduce at least one initial value of an adjustment parameter PR associated with said visuo-postural parameter.

The method then continues with a step E36 of adjusting a refraction-measuring apparatus depending on said initial value PR of the adjustment parameter.

The method then comprises a step E38 of measuring the refraction of the individual by means of said refraction-measuring apparatus such as it was adjusted in step E36. A current refraction value R is thus obtained for the individual (which value is an initial refraction value during the first passage through step E38).

The method continues with step E40, in which the individual is equipped by means of an item of vision-correcting test equipment suitable for correcting the current refraction R measured in the last passage through step E18.

As in the case of the embodiment described above with reference to FIG. 2, such an item of vision-correcting test equipment is for example a pair of vision-compensating spectacles such as described in document WO 2015/155456. In the case where a control module is used as described above with reference to FIG. 1, the control module for example transmits instructions to such vision-compensating spectacles in order that the latter generate a correction corresponding to the refraction measured during the last passage through step E38.

An additional step E42 of determining at least one additional value PP‴ of the aforementioned visuo-postural parameter is then passed to, the individual being equipped with the item of test equipment. The vision-testing device already mentioned as being used to implement step E2, and described below with reference to FIGS. 4 to 16, is for example used to do so.

The method may thus continue with an additional step E44 of processing said additional value PP‴ of the visuo-postural parameter in order to deduce at least one following value PR″ of the adjustment parameter associated with said visuo-postural parameter. This processing is of the same type as the processing of step E4 described above and will therefore not be described in detail here.

A step of comparing the initial value PR of the adjustment parameter and the following value PR″ of the adjustment parameter is then carried out in step E46.

When the comparison of step E46 indicates that the initial value PR and the following value PR″ differ by more than a predetermined difference threshold, the method loops to step E36 so as to implement steps E36 and E38 using the following value PR″ of the adjustment parameter to measure a new value of the refraction of the individual by means of the refraction-measuring apparatus adjusted depending on this following value PR″.

The new measured refraction value is then recorded as current refraction value R and the initial value PR is replaced with the following value PR″ of the adjustment parameter, then step E40 and the following steps are carried out again as described above.

When the comparison of step E46 in contrast indicates that the initial value PR and the following value PR″ differ by less than said predetermined difference threshold, said additional value PP‴ determined in step E42 and said current refraction value R (as measured in the last passage through step E38) are recorded as the results of the measuring method.

This refraction value R may then be used, in the context of an optical design method for designing an ophthalmic lens intended for this individual, to determine the optical profile of this ophthalmic lens (so that this optical profile allows the desired correction to be obtained, which correction is in particular defined by the refraction value R obtained using the method that has just been described).

Such an ophthalmic lens is particularly suited to the individual since the refraction measurement used to design the ophthalmic lens is carried out in a posture that is natural for the individual and in a situation in which the individual is wearing an item of vision-correcting equipment similar to that that he will finally have, the conditions of measurement of refraction in particular getting closer to the worn conditions by virtue of the possible iterations of the method.

As will be clear from the above description, a system comprising a vision-testing device suitable for evaluating said visuo-postural parameter of the individual, computing means suitable for deducing a value of an adjustment parameter from a value of the visuo-postural parameter of the individual evaluated by the vision-testing device, and a refraction-measuring apparatus suitable for being adjusted depending on said value of the adjustment parameter deduced by the computing means and for measuring the refraction of the individual, are used to implement the method for measuring the refraction of an individual in the embodiments proposed above.

As already indicated, one example of such a testing device is described below with reference to FIGS. 4 to 16. The refraction-measuring apparatus is for example for its part a phoropter such as described in document WO 2015/155458.

The computing means may be integrated into a control module (such as already mentioned above), optionally a dedicated control module. As a variant, as already indicated, the computing means may be integrated into the vision-testing device or the refraction-measuring apparatus.

In order to carry out the processing provided in particular in step E4 above, provision may be made to use a computer program suitable for carrying out the computations required for the processing of step E4 when this computer program is loaded into an executed by the aforementioned computing means.

The data obtained during the method described above (value of the visuo-postural parameter, measured refraction) may also be used to assist with the selection of a spectacle frame.

The visuo-postural-parameter values obtained in the context of the method described below with reference to FIGS. 6 to 16 may for example be used to deduce a minimum frame size in order to help the practitioner to recommend a frame.

In particular, it is possible by virtue of the determination of one or more visuo-postural parameters to deduce the final position of the near-vision point on an ophthalmic lens depending on the frame parameters. Depending on the desired or necessary progression length, it is therefore possible to make a recommendation as to the size of the frame, and more precisely as to the vertical size thereof (size known as "side B" in the optical field).

Thus, in the end, the individual will be able to wear a pair of spectacles comprising an ophthalmic lens designed by means of one of the aforementioned optical design methods and a spectacle frame selected as has just been described.

A vision-testing device usable to implement steps E2, E12, E22, E32 and E42 described above will now be described with reference to FIGS. 4 to 16.

Figure 4:
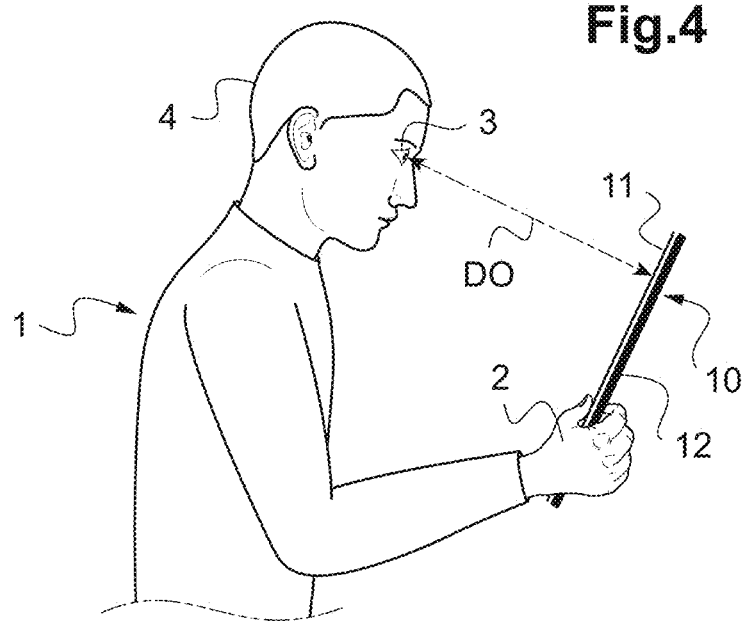
FIG. 4 is a schematic view of an individual holding in his hands a vision-testing device usable in certain steps of the aforementioned measuring method.

FIG. 4 shows an individual 1 whose visual behavior it is desired to test.

For this purpose, the individual 1 holds in his hands 2 a testing device 10 intended to determine this visual behavior under given conditions, and in particular the values of visuo-postural parameters defining this behavior.

More particularly here, it is desired to use the testing device 10 to analyze in a general manner the near vision of the individual 1, and in particular the visual behavior that he adopts when he is in a reading situation.

It will be considered that near vision corresponds to an observation distance DO (see FIG. 4) between the eye 3 of the individual 1 and the testing device 10 of smaller than 70 centimeters (cm).

In other embodiments, intermediate vision (DO lying between 40 cm and 4 meters) or far vision (DO greater than 4 m) may be tested by virtue of such a testing device.

The testing device 10 comprises (see FIGS. 4 and 5):
an active display 11 which displays a visually predominant target 20 at a plurality of target positions 30 aligned in at least two substantially parallel rows or columns, and a unit (not shown) for controlling the display 11, which unit is programmed so that the target positions 30 define, over time, a visual tracking protocol, so as to reproduce the movement of the gaze of the individual during reading.

The display 11 of the testing device may display, at any one time during the visual test, one single target or indeed a plurality of targets simultaneously. In both cases, the visually predominant target is a target that is suitable for catching the eye of the individual and that the individual will follow over the course of the visual test.

When a plurality of targets are displayed by the display 11, the visually predominant target may be, for example, a more luminous or more contrasted target, of different color or shape (round, square, star, . . . ), or of smaller or larger size than the others, or else a target which blinks whereas the other do not blink. The various targets displayed by the display may also comprise a set of indicators or indeed form a grid of grey dots.

In the embodiments where the display 11 displays only a single target 20 (case of FIG. 5), the latter may take a plurality of target positions 30 on the display 11. These target positions 30 "vary" in the sense that the target 20 moves sequentially from one target position 30 to another over the course of the visual test. Nevertheless, it will be noted that the sequence of target positions 30 successively adopted by the target 20 in these embodiments may comprise two identical target positions 30. In other words, it is possible during the visual test for the target 20 to return to a target position 30 already taken previously.

In the embodiments where the display displays a plurality of targets, one of which is visually predominant, the display positions of the targets may be variable over time, but in any event, the visually predominant target is the one which moves according to a sequence of target positions in such a way as to impose on the individual 1 a succession of particular gaze directions.

In the present description, "visual tracking protocol" will be intended to mean the display sequence of the visually predominant target 20 during the visual test carried out by the individual 1.

Stated otherwise, this visual tracking protocol corresponds to the succession, over time, of the target positions 30 taken by the visually predominant target 20. By virtue of this, a protocol is imposed on the individual 1 who gazes successively in a plurality of desired particular directions which are each associated with a particular target position 30 taken by the target 20. In this manner, if the target positions 30 of this target 20 are known, it is then possible, under certain conditions, to get back to the information relating to the gaze direction of the individual 1 during the visual test.

In the subsequent description, "gaze direction" of the individual 1 associated with a target position 30 of the target 20, will be intended to mean the direction of the straight line passing through:

one of the centers of rotation of the right eye or of the left eye of the individual 1, or a centroid of these centers of rotation; and said target position 30 when the individual 1 observes the target 20 taking this target position 30.

Figure 5:
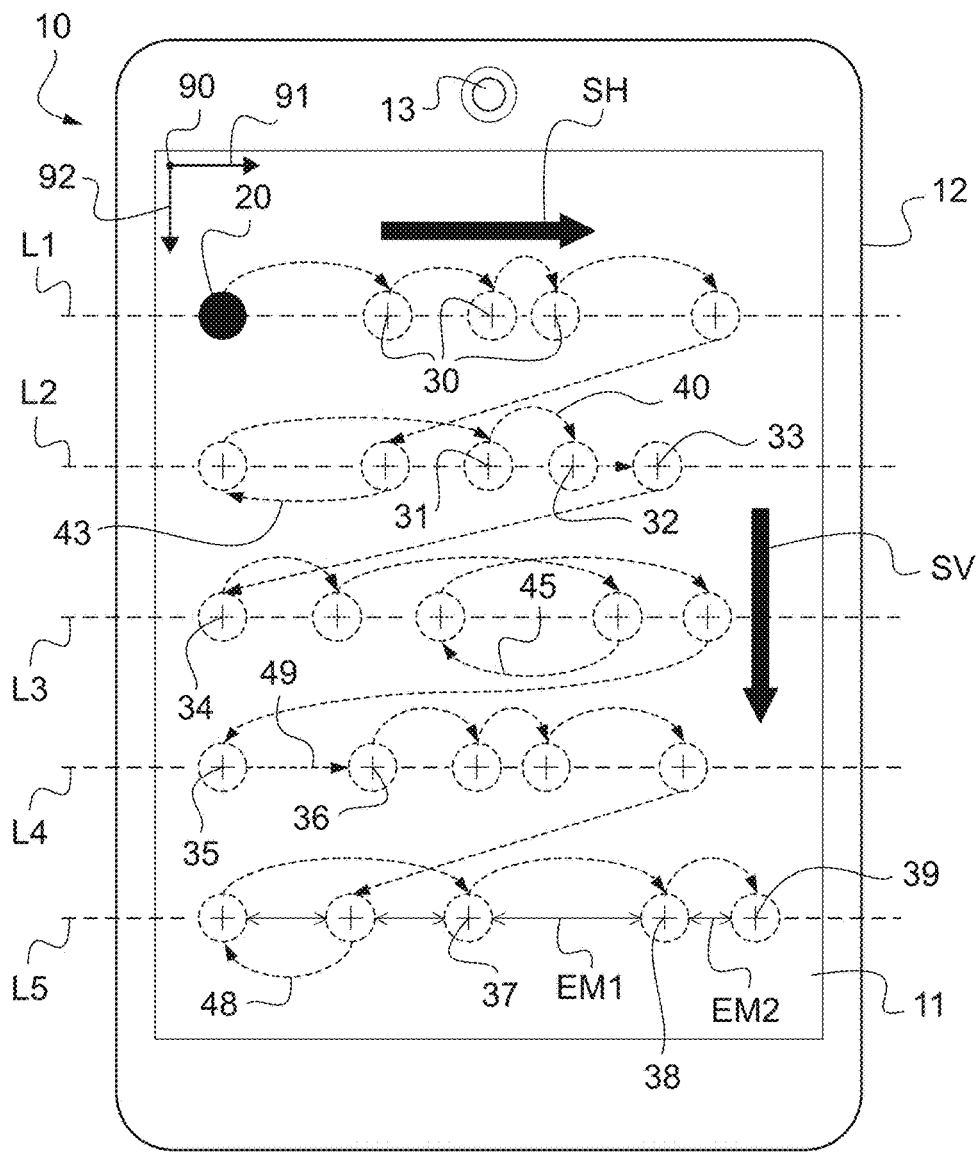
FIG. 5 is a face-on view of the testing device of FIG. 4, on which is displayed a visual target moving according to a visual tracking protocol.

As illustrated in FIG. 5, here the testing device 10 takes the form of a tablet computer. This tablet computer comprises a screen which constitutes the display 11 of the testing device 10. It also comprises a housing 12 surrounding the screen. The control unit of the testing device 10 corresponds, for its part, to the display controller for the tablet's screen 11 which is accommodated inside the housing 12.

The testing device 10 also comprises an image-capturing apparatus 13 which is driven by the control unit in a manner synchronous with the display 11 so as to trigger captures of images of the head 4 of the individual 1 observing the target 20 displayed by the display 11, each captured image corresponding to a predetermined target position 30.

Preferably, here the front camera 13 integrated into the tablet 10 is used as image-capturing apparatus of the testing device. This front camera 13 exhibits the advantage of always facing and sighting the individual 1 during the visual test performed by the individual 1.

In other embodiments, provision may be made to use an image-capturing apparatus which is separate and distinct from the display.

Here the target 20 comprises a luminous disk that is displayed on the screen of the tablet, the size of the target being sufficient for it to be seen by the individual 1 under the conditions of the visual test. Here, under reading conditions and in near vision (DO<70 cm), the target 20 has a characteristic size (e.g. diameter) of larger than 5 millimeters.

Advantageously, the characteristic size of the target 20 is determined in such a way that it may be seen with an acuity of larger than 0.1 tenths at 70 cm.

As a variant, the target may comprise a regular or irregular geometric pattern. It is preferably a question of any pattern except a symbol used by any writing system understood by the individual. In particular, the visually predominant target has no meaning to the individual. For example, the target is not a word that is intelligible to the individual.

The visual tracking protocol which is implemented by the testing device 10 and which is intended here to simulate the reading of a text by the individual 1 will now be described with reference to FIG. 5.

Advantageously, the display of the target according to the visual tracking protocol implemented by the testing device 10 constitutes a visual stimulus for the individual 1, intended to make him move his eyes 3 by tracking this target 20 according to the same scheme as that which the individual 1 would adopt if he were actually reading a text.

Stated otherwise, the display of the visually predominant target 20 on the display 11 is controlled in such a way that, when the individual 1 follows with his gaze the target 20 from one target position 30 to another, the direction of the gaze of the individual 1 exhibits successive gaze directions which are entirely similar to the gaze directions that this individual 1 would have when reading a text.

The sequence of the target positions 30 taken successively by the visually predominant target 20 is preferably predetermined depending on a reference text, and/or on a reading model, corresponding to the characteristics and/or to the reading/writing preferences of the individual.

For example, the sequence may be determined beforehand with another device, during a calibration operation in which the individual is asked to choose a reference text from among a plurality of available actual texts and to read it aloud. The reading speed may then serve as parameter for determining the display positions of the target.

The sequence may also be predetermined depending on the individual's age or depending on a reading level declared by the individual, subsequent to a questionnaire filled in by the individual.

It is also possible to envisage doing a training run with an average speed, asking the individual if this average speed was too fast or not fast enough and adjusting the speed depending on his response.

It will be observed firstly that the reading of a text by an individual is done naturally according to a reading scheme comprising three distinct operations: fixations, saccades and reverse saccades.

During fixations, the individual deciphers the word that he is in the process of reading, that is to say the word on which the individual's gaze is fixated.

During saccades, corresponding to the phases of movement, that is to say to passing from the reading of one word to the following word, the individual's eyes move rapidly so as to pass from one fixation to another.

These saccades are related to the visual span, that is to say to the number of characters (letters, symbols, ideograms, etc.) which are decipherable for a given fixation. They allow the reader to decipher all the characters of a text.

The saccades generally take place in the direction of reading of the text. Nonetheless, the eyes also perform very fast "reverse saccades" in the direction opposite to the direction of reading so as to pass from one fixation to another. This movement is induced by an error of the oculomotor muscles or by poor reading and understanding of the text.

One of the advantages of the testing device 10 is to propose visual tracking protocols which come as close as possible to the individual's reading schemes.

The testing device 10 therefore makes it possible to simulate, simply, the reading of a text and to place the individual in a situation in which he will adopt a natural posture close to that which he would adopt for reading in near vision.

A determination of the visual behavior of the individual under these conditions is therefore more precise and the optical design of an ophthalmic lens intended for the individual may be improved so that the design of the ophthalmic lens meets the individual's visual needs.

Preferably, the target positions 30 of the target 20 are aligned in at least two substantially parallel lines. More precisely, in the example embodiment shown in the figures, the unit for controlling the display 11 is programmed so that the successive target positions 30 of the target 20 are aligned with five rows L1, L2, L3, L4, L5 (see FIG. 5).

Alternatively, the target positions of the target may be aligned in at least two columns.

Generally, the target positions 30 of the target 20 may define parallel lines of arbitrary direction, in particular substantially horizontal or vertical for the individual 1.

Preferably again, each row, or alternatively each column, comprises at least three aligned positions of said target (case of the positions 37, 38, 39 for the row L5 of FIG. 5).

In order for the visual tracking protocol to represent the way in which the wearer reads as well as possible, provision will advantageously be made for the visual tracking protocol to describe a reading trajectory that accords with that defined by a given writing system, so as to reproduce the way in which the gaze of the individual moves when he reads in accordance with the writing system.

The reading trajectory may be defined here as the path, on the display 11, scanned by the gaze direction of the individual 1 when he looks at the sequence of target positions 30 adopted by the visually predominant target 20.

The reading scheme adopted by an individual is related not only to the nature or to the specific properties of the text, but also to the specific features of each type of writing.

It will be noted moreover that the various types of writing may be classified in a functional manner (alphabetic, syllabic or logographic writing) and a directional manner (horizontal and vertical direction of writing and/or reading).

Provision is therefore made in the testing device for the control unit to store in memory a favored vertical SV and horizontal SH direction of travel (see FIG. 5) of the visual tracking protocol.

This favored vertical and horizontal direction of travel is determined beforehand depending on the characteristics of the individual, and in particular his ability to read a text according to a given writing system.

For example, when the testing device is used by a French person who reads from left to right and from top to bottom, the horizontal direction of travel stored by the control unit is a direction of travel going from the left of the screen 11 to the right of the screen 11, and the vertical direction of travel stored by the control unit is a direction of travel going from the top of the screen 11 to the bottom of the screen 11.

Hence, in a preferred embodiment, the substantially parallel rows L1, L2, L3, L4, L5 along which the target positions 30 of the target 20 are aligned extend substantially horizontally, the direction of travel of the visual tracking protocol being identical for all the rows taken successively from the topmost to the bottommost, from left to right (or from right to left for right-to-left writing such as Arabic or Hebrew).

In the same manner, when the testing device is used by a Mongolian, who reads from top to bottom and from right to left, the vertical direction of travel stored by the control unit is a direction of travel going from the top of the screen to the bottom of the screen, and the horizontal direction of travel stored by the control unit is a direction of travel going from the right of the screen to the left of the screen.

Hence, in an embodiment suitable for this writing system, the substantially parallel lines along which the predetermined positions of the target are aligned extend substantially vertically, the direction of travel of the visual tracking protocol being identical, from top to bottom or from bottom to top, for all the lines taken successively from right to left.

Advantageously, the control unit of the testing device 10 is programmed to allow the visual tracking protocol to be selected from a plurality of visual tracking protocols recorded in a local or remote database, in which a direction of travel is recorded in association with the visual tracking protocol to which it corresponds.

Thus, the individual depending on his own reading and/or writing characteristics may choose the visual protocol which corresponds to him, so that he is under natural reading-like conditions whilst carrying out the visual test. It is then certain that his reading mechanisms and strategies are put in place so as to recover the posture which is most representative of the use of his near vision.

In order to reproduce the reading scheme such as described above, with fixations, saccades and reverse saccades, provision is made for the control unit of the display 11 to display the target 20 according to a preferential visual tracking protocol.

Hence, provision is made for the control unit to require, in each target position 30 of the visual tracking protocol, that the target 20 be displayed for a predetermined duration. What is meant by this is that the target 20 is kept displayed fixedly on the screen in such a way that the individual 1 is forced to fix his gaze on the target 20, this corresponding to one fixation on the target position 30 in the reading trajectory of the individual 1.

Advantageously, the target 20 is fixated for the predetermined duration, that is to say that the target position 30 of the target 20 does not change for this predetermined duration, before passage to the following target position of the reading trajectory.

Preferably, this predetermined duration lies between 50 milliseconds and 1 second, this corresponding typically to standard fixation times.

The predetermined duration may also vary over the course of the reading trajectory, this accounting for the fact that the fixation of the gaze of the individual 1 on a word during actual reading may depend on the word (size, length) and on the level of understanding of this word (poorly known or unknown word, nearly indecipherable word or character, poorly spelled word, etc.).

Advantageously also, provision is made for the control unit to impose a predetermined lag between the displays of the target 20 in two successive target positions (see for example the target positions 31, 32 in FIG. 5) of the visual tracking protocol.

In this manner, it is possible to simulate by virtue of the testing device 10 the saccades or reverse saccades existing along the reading trajectory of the individual 1. As above, provision may be made for the control unit to make the predetermined lag vary during the visual tracking protocol.

This makes it possible to allow for the fact that the reading speed of the individual 1 may vary during the reading of a text.

This also makes it possible to envisage the cases where the gaze direction of the individual 1 passes from one line to another, as is the case for example from the target position 33 to the target position 34 of FIG. 5, jumping to the start of the next line requiring more time in so far as the variation in the gaze direction of the individual 1 is larger.

It is then possible to provide two cases for the target during the predetermined lag.

In one embodiment, provision may be made for the target to be invisible during the predetermined lag. This corresponds to the case of the target positions 31 and 32 of FIG. 5 in which the target 20 "jumps" (the jump being represented by the dashed arrow 40) from the position 31 to the following position 32. This embodiment makes it possible to allow for the gaze of the individual that jumps from word to word while reading a text.

In an alternative embodiment, provision may be made for the target to be visible during the predetermined lag and to move between the two corresponding successive target positions of the visual tracking protocol, from one to the other. This corresponds to the case of the target positions 35 and 36 where the target moves (the movement being represented by the dotted arrow 49), while remaining visible.

Advantageously, the testing device 10 of the invention is such that the control unit requires that two successive target positions 37, 38, 39 of the visual tracking protocol be separated by a distance EM1, EM2 of less than 10 centimeters. In this manner, during the visual test, there is no need for the individual 1 to vary his gaze direction in a way that would cause him to exert himself, as is generally the case when reading.

Preferentially, provision is moreover made for the control unit to require that the distance EM1, EM2 separating two successive target positions 37, 38, 39 of the visual tracking protocol varies along the visual tracking protocol. This makes it possible to adapt the separation between the targets 20 displayed depending on the average span of the words for a given writing system.

In another embodiment, the control unit is programmed so that the display of the target 20 in two successive target positions of the visual tracking protocol follows the favored direction of travel, horizontal and/or vertical, at least six times out of ten. This is illustrated in FIG. 5 in which directions of travel have been represented in the visual tracking protocol, these directions of travel being represented by the dashed arrows 43, 45, 48, which go not from left to right like the favored horizontal direction of travel SH, but from right to left.

It is thus possible by virtue of this to simulate the reverse saccade movements previously described while the individual 1 is reading a text. Indeed, here four times out of ten, the movement of the eyes 3 of the individual 1 following the target 20 of the gaze between two successive target positions 30 takes place in the direction opposite to the favored direction of travel.

Just as for the saccade movements detailed above, the target 20 may pass from one target position to the following target position, in a direction of travel opposite to the favored direction of travel, either by jumping from one position to the other (invisible target), or by moving from one to the other (visible target).

A procedure for determining at least one visual behavior parameter of the individual 1 or visuo-postural parameter will now be described with reference to FIGS. 6 to 16, this procedure using the testing device described above, which is particularly suitable for the implementation of this procedure.

The determining procedure comprises the following steps:
 a step of requesting the individual to perform a visual test during which he observes at least one target position,
 a step of measuring a datum representative of at least one gaze direction of the individual during said visual test,
 a step of determining a reference gaze direction, depending on said measured representative data,
 a step of positioning, with respect to said reference gaze direction, at least one measured target position which is determined depending on said datum representative of said gaze direction of the individual measured during the visual test.

Advantageously, a step of deducing, depending on said at least one measured target position, the one or more sought-after visuo-postural parameters is carried out, after the positioning step.

In practice, the tablet 10, or a local or remote computer, is programmed to accomplish the above steps detailed below.

Preferably, in the requesting step of the determining procedure, the individual 1 successively observes various target positions 30.

The individual 1 is therefore requested to observe the screen 11 of the tablet 10 which displays the visually predominant target 20 in a predetermined sequence of target positions 30 of the chosen visual tracking protocol such as described above with reference to FIG. 5.

According to a first variant embodiment, the determining procedure comprises following intermediate steps:
 said gaze directions of the individual are determined during the visual test in a frame of reference tied to the head of the individual,
 the coordinates of said target positions are determined in said frame of reference tied to the head of the individual, and
 a centroid of said target positions in the frame of reference tied to the head of the individual is determined, on the basis of said coordinates, and
 said reference gaze direction is defined as a straight line linking a center of rotation of a left eye or right eye of the individual, or a centroid of said centers of rotation, to said centroid of the target positions in the frame of reference tied to the head of the individual.

As coordinate system tied to the head 4 of the individual 1, it is for example possible to choose a coordinate system termed the "primary gaze coordinate system" or "CRO frame of reference", in which the head 4 of the individual 1 has a fixed position and orientation and with which a preferably orthonormal frame of reference, having an origin and three untied axes, is associated.

Figure 6:
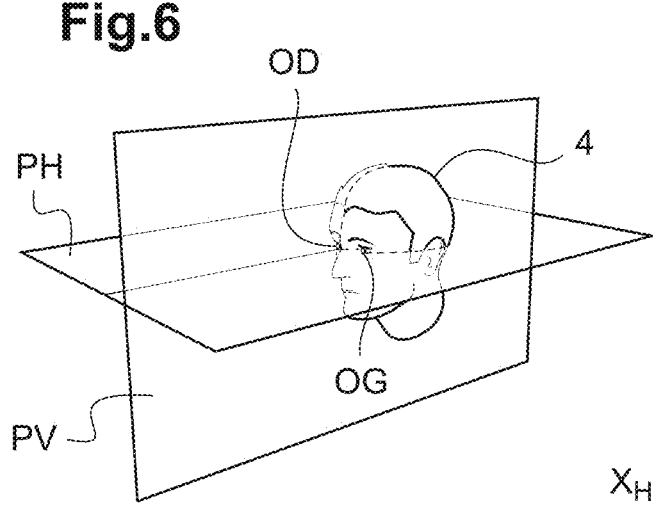
FIG. 6 is a schematic view of the head of the individual and of various planes associated with this head.
Figure 7:
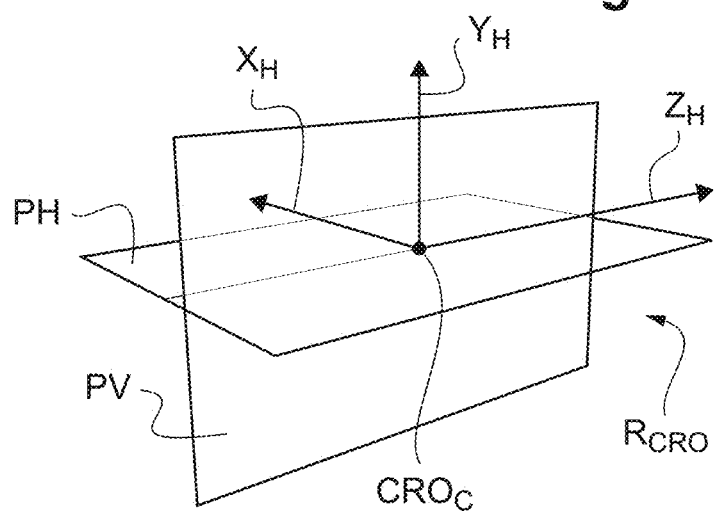
FIG. 7 shows a frame of reference tied to the head of the individual.

FIGS. 6 and 7 illustrate how this CRO frame of reference is constructed.

In particular, FIG. 6 shows a vertical plane PV corresponding to a sagittal plane of the head 4 of the individual 1, which is the vertical plane passing through a perpendicular bisector of the two eyes of the individual 1, i.e. the right eye OD and left eye OG.

This perpendicular bisector of the eyes OD, OG is an axis which passes through the middle of a segment which is defined by the center of rotation of the right eye OD (referenced CROD below) and the center of rotation of the left eye OG (referenced CROG below) and which is parallel to the Frankfurt plane of the head 4 of the individual 1.

The Frankfurt plane of the head of the individual is defined as the plane passing through the lower orbital points of the individual 1 and the porion of the individual 1, the porion being the auditory canal's highest point of the skull, which corresponds to the tragion of the ear. For the determination of the Frankfurt plane, it is considered that the individual is in an orthostatic position, in which he exerts minimum effort. This position corresponds to a natural posture, referred to as the "primary gaze posture" below.

In this natural position, the gaze direction of the individual is then the primary gaze direction, that is to say that he gazes straight ahead. The Frankfurt plane is then generally horizontal.

Moreover, a plane PH which contains the centers of rotation CROD, CROG of the eyes OD, OG of the individual 1 is defined (see FIG. 6).

In the particular example described here, this plane PH is parallel to the Frankfurt plane of the head 4 of the individual 1 and is therefore horizontal.

On the basis of the primary gaze posture of the individual 1, that is to say of knowledge of the orientation of the Frankfurt plane, and of the centers of rotation CROD, CROG of the eyes OD, OG of the individual 1, it is possible to construct the CRO frame of reference tied to the head 4 of the individual 1, referenced $R_{CRO}$ below, by choosing:
 as origin one of the centers of rotation CROD, CROG of the right eye OD or of the left eye OG of the individual 1 or a centroid of these centers of rotation CROD, CROG;
 a first axis parallel to a primary gaze direction of the individual 1;
 a second axis that is horizontal and perpendicular to the first axis, and
 a third axis that is perpendicular to the first axis and to the second axis.

In the described example embodiments, the origin of the frame of reference $R_{CRO}$ is chosen as being the point situated in the middle of the segment joining the center of rotation CROD of the right eye OD and the center of rotation CROG of the left eye OG of the individual 1. In other words, this origin point, designated "cyclops CRO" and referenced $CRO_C$ below, corresponds to the centroid of the centers of rotation CROD, CROG of the eyes OD, OG of the individual 1.

The three axes $X_H$, $Y_H$, $Z_H$ of the frame of reference $R_{CRO}$ are also shown in FIG. 7.

The axis $X_H$ (second axis) passes through the cyclops CRO, $CRO_C$ and is oriented here from the left center of rotation CROG to the right center of rotation CROD. The axis $X_H$ is horizontal here since it is contained in the horizontal plane PH parallel to the Frankfurt plane. An opposite orientation is also possible.

The axis $Z_H$ (first axis) is parallel to the primary gaze direction when the individual 1 is in a natural position, that is to say in the primary gaze posture. In the particular case described here, the axis $Z_H$ is situated in the vertical plane PV of the head 4 of the individual 1 and is parallel to the Frankfurt plane. In other cases where the head of the individual exhibits an angle of yaw, this axis $Z_H$ might not be situated in the vertical plane. The axis $Z_H$ extends here in a direction away from the head 4 of the individual 1 (towards the rear).

The axis $Y_H$ (third axis) extends, for its part, in the vertical sagittal plane PV of the head 4 of the individual 1 and is perpendicular to the Frankfurt plane. The axis $Y_H$ is therefore indeed perpendicular to the axis $X_H$ and to the axis $Z_H$. It is oriented upwards here, so that the frame of reference $R_{CRO}$ is direct.

It will be noted that the frame of reference $R_{CRO}$ is tied to the head 4 of the individual 1 and that therefore this frame of reference $R_{CRO}$ shifts with the head 4 of the individual 1, the position and the orientation of this frame of reference $R_{CRO}$ changing with respect to an absolute frame or a frame of reference (for example a frame of reference tied to the room in which the individual performs the visual test) which would not be tied to the head 4 of the individual 1 depending on the movements of the head 4 of the individual 1.

It will be noted that the determination of the positions of the centers of rotation CROD, CROG may be carried out according to the principle known per se and described for example in document FR 2914173, an equivalent of which in English is document US 2010/0128220.

During this determination of the centers of rotation CROD, CROG, the individual 1 wears, on his head 4, fastened to the head 4, a tagging system (metrological reference) or "clip" which comprises tagging elements (markers) detectable during an image capture of the head 4 of the individual 1.

To summarize, at least two images of the head 4 of the individual 1 are captured by means of an image-capturing apparatus:
 a first image when the individual gazes at the image-capturing apparatus while being positioned face-on, gazing straight ahead into the far distance (primary gaze posture), and
 a second image when the individual gazes at the image-capturing apparatus while being positioned three-quarters-on.

On the basis of processing of the two captured images (see document FR 2914173), the positions of the centers of rotation CROD, CROG are deduced in a coordinate system tied to the tagging system.

It is then possible to determine the "cyclops" center of rotation, which is the centroid of the two previously determined centers of rotation CROD, CROG.

For the determination of the primary gaze posture, the positions of the centers of rotation CROD, CROG are reused together with the first image captured face-on. Provision may also be made to compensate for the inclination of the tablet 10 during the latter determination.

Figure 8:
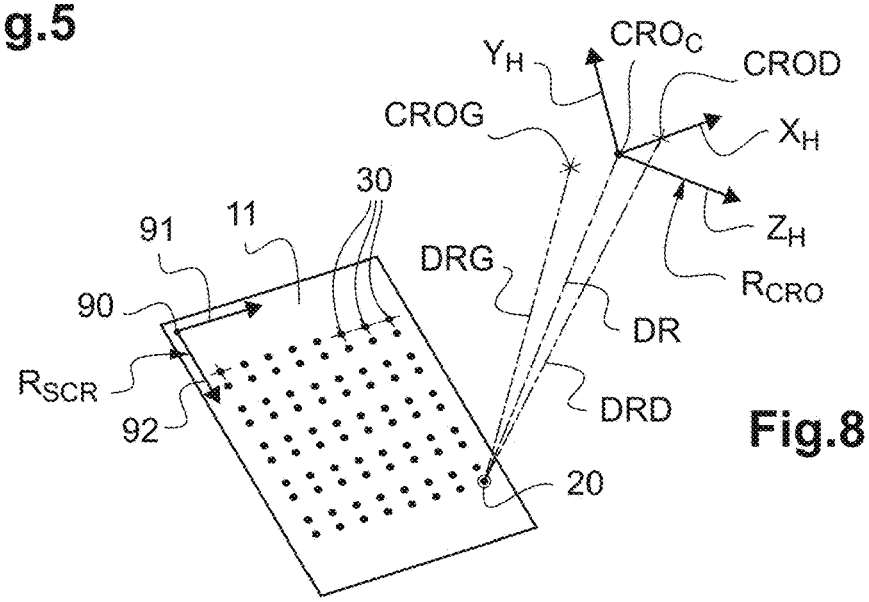
FIG. 8 shows a display of the testing device of FIG. 4 with a displayed target and a frame of reference tied to the head of the individual looking at the target in a final position of the protocol.

FIG. 8 shows the gaze direction DR joining the cyclops CRO to the target 20, which is here positioned on the last target position of the visual tracking protocol, as well as the frame of reference $R_{CRO}$ tied to the head 4 of the individual 1 with its three main axes $X_H$, $Y_H$, $Z_H$.

FIG. 8 also shows the gaze directions referenced respectively DRD and DRG corresponding to the gaze directions for the right eye OD and left eye OG of the individual 1.

Once the frame of reference tied to the head 4 of the individual 1 has been chosen, here the frame of reference $R_{CRO}$, it is possible to determine, for each target position 30 of the target 20 observed on the screen 11 of the tablet 10, the coordinates of these target positions in this frame of reference $R_{CRO}$.

For this purpose, during the measuring step of the determining procedure:
 images of a part of the head 4 of the individual 1 observing each target position 30 are captured by means of the front camera 13, turned towards the head 4 of the individual 1, of the testing device 10, each target position 30 being able to be predetermined in a frame of reference tied to the front camera 13,
 these images are stored in association with the coordinates, expressed in this frame of reference tied to the front camera 13, of the target position 30 observed by the individual 1, and
 the coordinates of the frame of reference $R_{CRO}$ tied to the head 4 of the individual 1 in the frame of reference tied to the image-capturing apparatus 13 or the coordinates of the gaze directions DR of the individual 1 in the frame of reference $R_{CRO}$ tied to the head 4 of the individual 1 are determined on the basis of the captured images and of the associated coordinates of the observed target position 30.

A frame of reference tied to the front camera 13 may be for example the frame of reference $R_{SCR}$ of the screen 11 (see FIG. 5 for example) having as origin the top left corner 90 of the screen 11 and as axes the two mutually perpendicular axes 91, 92 directed along the columns and the rows of the screen 11.

Advantageously, the front camera 13 triggers an image capture of the head 4 of the individual 1 with a capture offset with respect to the moment at which the target 20 is displayed at the predetermined target positions 30 of the visual tracking protocol on the screen 11. This offset may be zero, or else preferably small, for example less than 200 milliseconds. This makes it possible to take into account the reaction time of the individual 1 and the time he takes to move his eyes 3 when the position 30 of the target 20 on the screen 11 changes.

According to a variant, the front camera may also carry out a continuous video sequence, for example at a rate of twenty images per second, and extract from the video sequence the best image giving the best information on the visual behavior of the individual during the display of the target at the corresponding target position.

Each image captured by the front camera 13 of the tablet 10 thus corresponds to a predetermined target position 30 of the visually predominant target 20, the position 30 of which in the frame of reference $R_{SCR}$ tied to the image-capturing apparatus 13 is perfectly known.

To determine the coordinates of the frame of reference $R_{CRO}$ tied to the head 4 of the individual 1 in the frame of reference tied to the image-capturing apparatus 13 or the coordinates of the gaze directions DR of the individual 1 in the frame of reference $R_{CRO}$ tied to the head 4 of the individual 1, provision is made for means for processing images of the tablet 10, which consist for example of the processor of the tablet 10, which detects in the captured images of the head 4 of the individual 1 the markers of the clip worn by the individual 1 on his head 4.

The position and the orientation of the clip in the frame of reference $R_{SCR}$ tied to the front camera 13 are then determined for each captured image, that is to say for each target position 30 of the target 20 of the visual tracking protocol, for example by using the method described in document US 2010/0128220.

The positions of the centers of rotation CROD, CROG of the eyes of the individual 1 with respect to the clip being known, the position (spatial coordinates) and the orientation (angular coordinates) of the frame of reference $R_{CRO}$ tied to the head 4 of the individual 1 are also known with respect to the clip.

This is moreover illustrated in FIG. 8 in which the frame of reference $R_{CRO}$ has been shown with its origin at the cyclops center of rotation $CRO_C$ (centroid of the centers of rotation CROD, CROG) and its axes $X_H, Y_H, Z_H$.

Thus, through a change of frame of reference, it is possible to determine, for each target position 30 of the target 20 of the visual tracking protocol, the position and the orientation of the frame of reference $R_{CRO}$ tied to the head 4 of the individual 1 in the frame of reference $R_{SCR}$ tied to the front camera 13 of the tablet 10.

It is also possible to determine, for each target position 30 of the target 20 of the visual tracking protocol, the gaze directions DR of the individual 1 in the coordinate system $R_{CRO}$ tied to the head 4 of the individual 1, these gaze directions DR here joining the cyclops center of rotation $CRO_C$, origin of the frame of reference $R_{CRO}$ tied to the head 4 of the individual 1, to the target 20.

It is finally possible to re-express, on the basis of the positions and orientations of the head 4 or of the gaze directions DR of the individual 1, the target positions 30 of the target 20 in the frame of reference $R_{CRO}$ tied to the head 4 of the individual 1.

These target positions 30 in the frame of reference $R_{CRO}$ tied to the head 4 of the individual 1 are data representative of the measured gaze directions DR of the individual 1 during the visual tracking protocol.

It is thus possible to determine, after the measuring step, a reference gaze direction depending on these representative data.

In certain embodiments, the reference gaze direction corresponds to a direction of observation of the individual of a distant target (far vision) when the individual is in a natural posture.

In the embodiment described here, the reference gaze direction is an average gaze direction of the individual 1 during the visual test.

Figure 9:
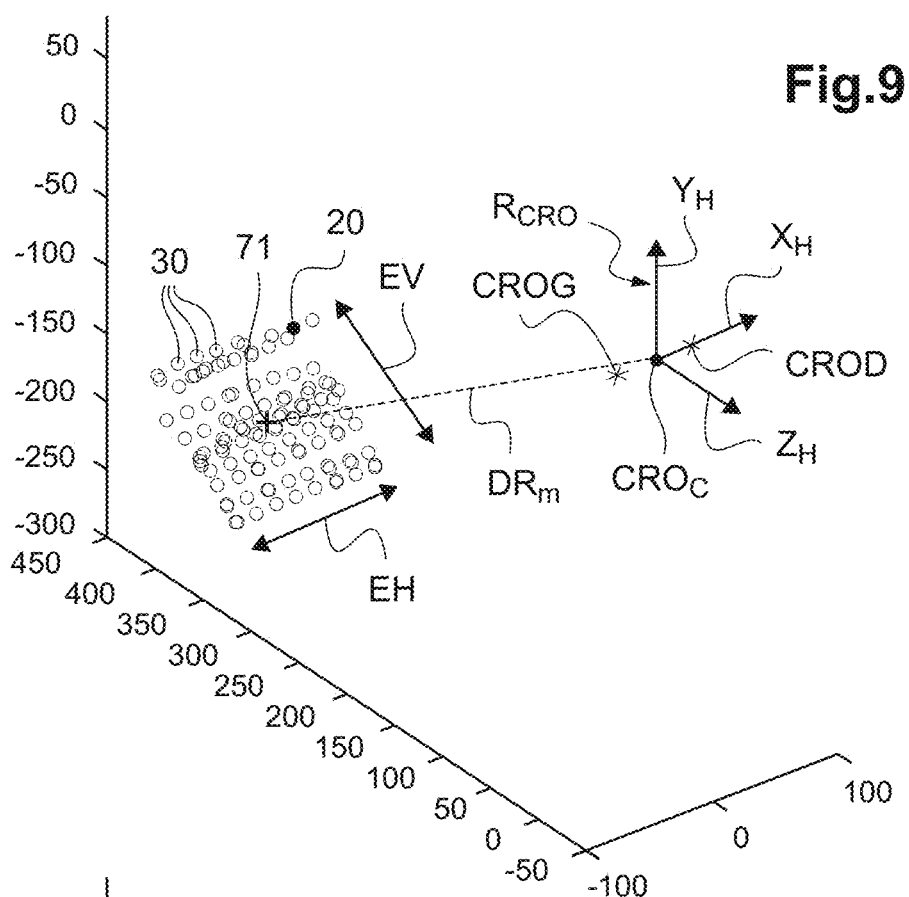
FIGS. 9 and 10 show examples of measured positions of the target in the coordinate system tied to the head of the individual during the reading protocol.
Figure 10:
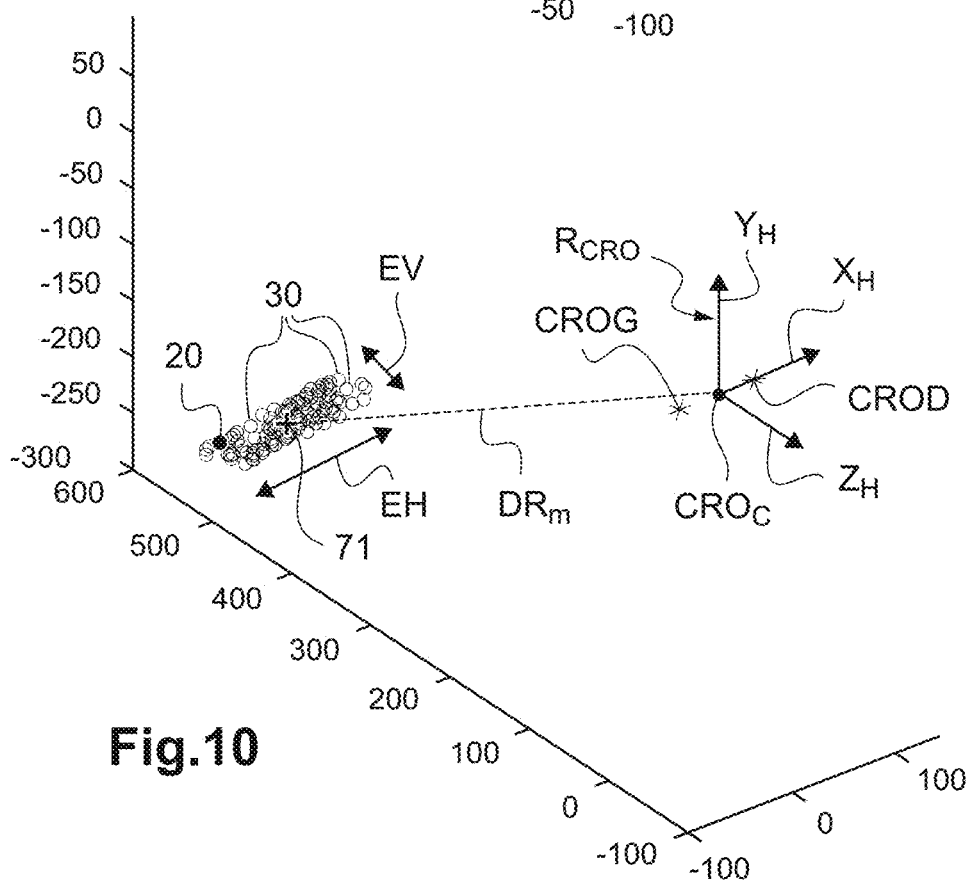

As shown in FIGS. 9 and 10, this average gaze direction, referenced $DR_m$ below, is preferably chosen to be the straight line linking the cyclops CRO, $CRO_C$, to the centroid 71 of the target positions 30.

As a variant, the average gaze direction may be defined on the basis of the right center of rotation CROD, of the left center of rotation CROG, of the center of rotation of the master eye, or indeed of the center of rotation of the dominant eye.

As a further variant, the average gaze direction is chosen here as being the straight line linking a center of rotation of the left eye or right eye of the individual, or a centroid of said centers of rotation, to a target position in the frame of reference tied to the head of the individual.

Given not only that the position and the orientation of the head 4 of the individual 1 changes during the visual test protocol with respect to the frame of reference $R_{SCR}$ tied to the image-capturing apparatus 13 but also that the individual 1 modifies the position and orientation of the tablet 10 during the visual test, it will be understood that the target positions 30 of the target 20 in the frame of reference $R_{CRO}$ tied to the head 4 of the individual 1 provide information on the visual behavior of the individual 1, in particular on his propensity to move his eyes 3 while reading a text.

Indeed, if the individual 1 follows the visual tracking protocol while greatly modifying his gaze direction DR, then the target positions 30 of the target 20 in the frame of reference $R_{CRO}$ tied to the head 4 of the individual 1 are arranged in a relatively similar way to the target positions 30 of the target 20 in the frame of reference $R_{SCR}$ tied to the front camera 13. This is the case in FIG. 9.

Conversely, if the individual 1 follows the visual tracking protocol while maintaining an almost fixed gaze direction DR, then the target positions 30 of the target 20 in the frame of reference $R_{CRO}$ tied to the head 4 of the individual 1 are grouped together. This is the case in FIG. 10.

The determining procedure moreover comprises a step of positioning, with respect to the reference gaze direction $DR_m$, measured target positions 50 (see FIG. 11) that are determined on the basis of the gaze directions DR of the individual 1 measured during the visual test, when the individual 1 follows the target positions 30 of the target 20 that are placed on the screen 11 of the tablet 10.

Preferably, during this positioning step, a dummy display surface 111 oriented, with respect to the reference gaze direction $DR_m$, according to an average orientation of the screen 11 during the visual test, is also determined.

The average orientation may for example take account of the average angles of inclination and/or of pitch with which the individual 1 holds the tablet 10 between his hands 2 during the visual test.

Figure 11:
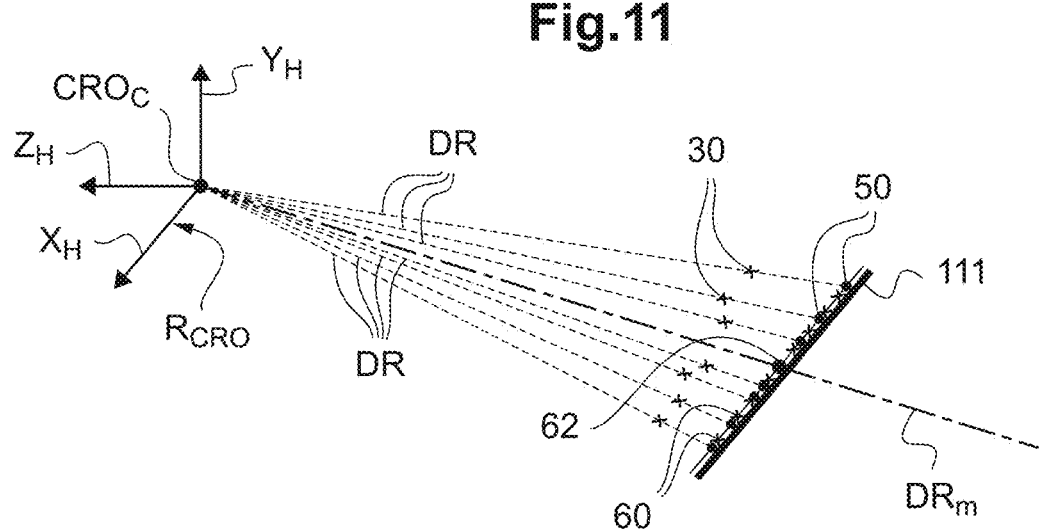
FIG. 11 is a conceptual diagram showing a reference gaze direction in a coordinate system tied to the head of the individual and a dummy display surface for the theoretical target positions.

As shown in FIG. 11, the measured target positions 50 (symbols '.' in FIG. 8) are also determined, in the positioning step, to be the intersections of the gaze directions DR of the individual 1 during the visual test and of the dummy display surface 111.

Stated otherwise, the measured target positions 50 correspond to the projections of the target positions 30, along the gaze directions DR associated with these target positions 30.

In a preferred embodiment, the determining procedure comprises an additional positioning step.

During this additional positioning step, theoretical target positions 60 (symbols "+" in FIG. 8) the relative positions of which with respect to one another are identical to the relative positions of the target positions 30 on the display surface 11 (screen) of the tablet 10, are positioned with respect to the reference gaze direction, here the average gaze direction $DR_m$.

Preferably, these theoretical target positions 60 are positioned so that their centroid 62 lies on the reference gaze direction $DR_m$.

Figure 12:
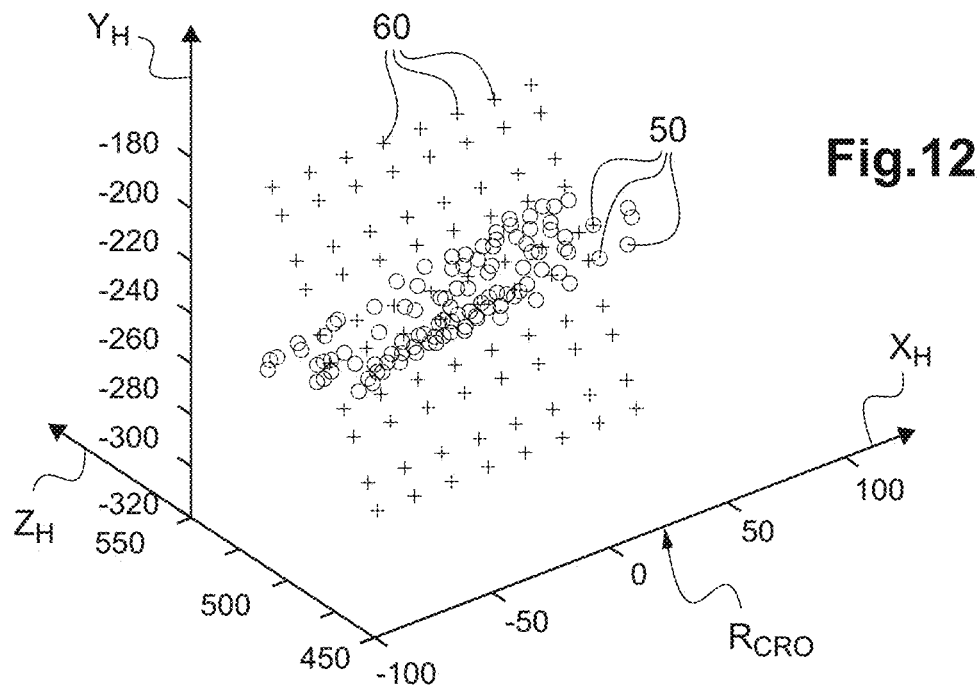
FIG. 12 shows, in the coordinate system tied to the head of the individual, the theoretical target positions on the display surface and the target positions measured in this coordinate system.

Thus, on completion of the positioning steps described above, the coordinates of the measured target positions 50, and the coordinates of the theoretical target positions 60, in the frame of reference $R_{CRO}$ tied to the head 4 of the individual 1, have been determined on the dummy display surface 111. This is illustrated in FIG. 12 of the drawings.

Visual behavior parameters of the individual 1 during the visual tracking protocol may be deduced from the measured target positions 50 and from the theoretical target positions 60.

Indeed, it is already possible to determine a first visual behavior parameter corresponding to the position (coordinates) of the near-vision behavior (NVB) centroid of the target positions 30 in the frame of reference $R_{CRO}$ tied to the head 4 of the individual 1. This NVB centroid provides information in particular on the average gaze direction $DR_m$ of the individual 1 (cf. above) during the visual test.

Moreover, as explained above with reference to FIGS. 9 and 10, it will be understood that the distribution (position and spread) of the measured target positions 50 with respect to the theoretical target points 60, the distribution of which over the dummy display surface 111 is set by that of the target positions 30 on the screen 11, provides information on the tendency of the individual 1 to move his head 4 and/or his eyes 3 during a reading task.

Thus, in another embodiment described with reference to FIGS. 13 to 16, the deducing step of the determining procedure preferably comprises a comparison of the theoretical target positions 60 and of the measured target positions 50 in the frame of reference $R_{CRO}$ tied to the head 4 of the individual 1. This comparison makes it possible to deduce one or more sought-after visual behavior parameters, in particular visual behavior parameters of the individual 1 that are representative of the vertical spread EV and of the horizontal spread EH (see FIG. 6) of the target positions 30 in the frame of reference $R_{CRO}$ tied to the head 4 of the individual 1. The vertical spread EV, respectively the horizontal spread EH, is indeed representative of the propensity of the individual 1 to move his eyes downwards (or upwards), respectively from left to right (or from right to left), during the visual task.

In a preferred embodiment, this comparison may comprise the determination of disparities between the theoretical target positions 60 and the measured target positions 50 in a favored direction of the dummy surface 111. This is illustrated in FIGS. 13 to 16.

Figure 13:
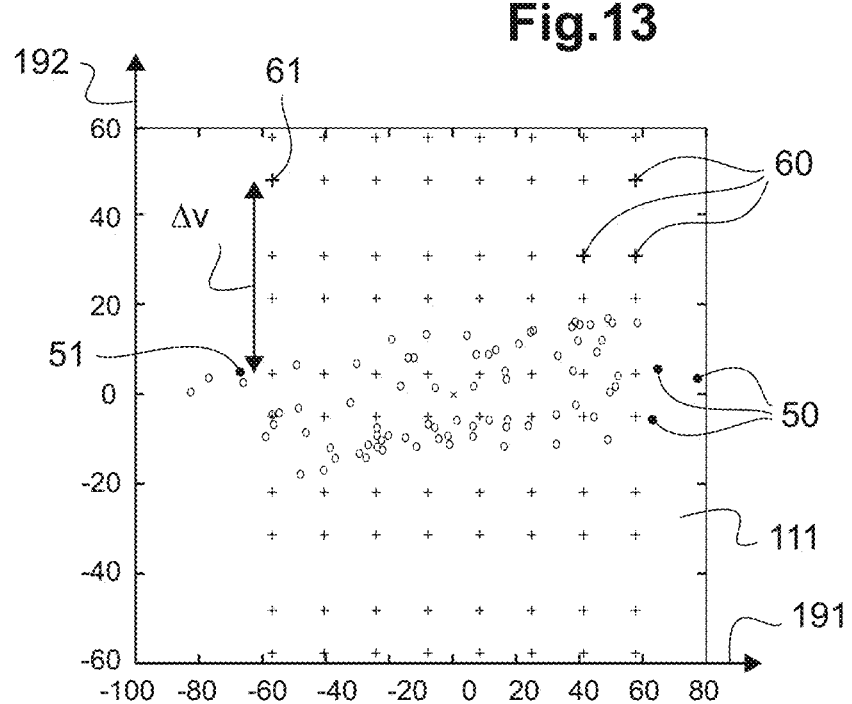
FIG. 13 is a graph illustrating the computation of the disparity between the theoretical target positions and the measured target positions.
Figure 14:
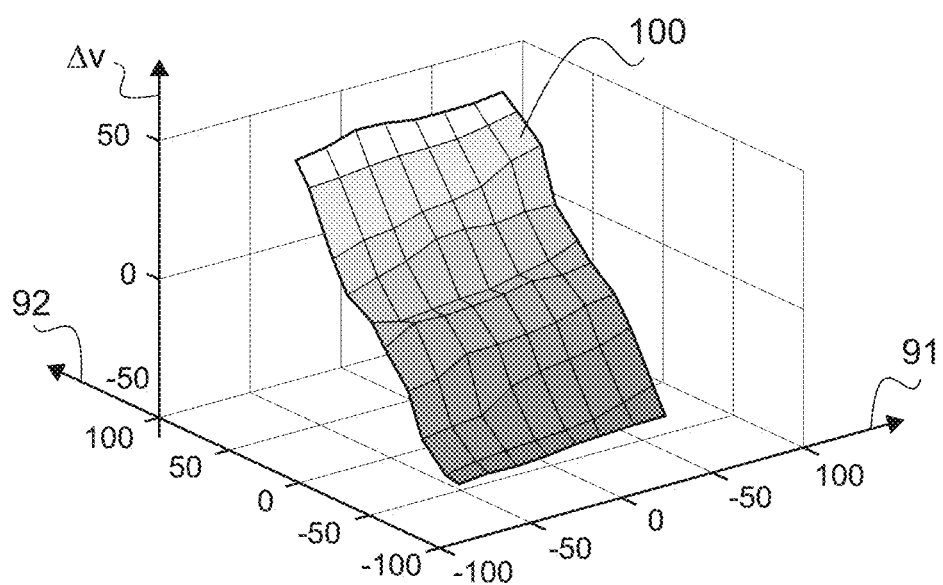
FIG. 14 is a curve representative of the disparities between the theoretical target positions and the measured target positions as a function of the theoretical target positions.

In particular, FIG. 13 shows the dummy display surface 111 endowed with axes 191, 192 oriented and normed in an identical manner to the axes 91, 92 of the screen 11 (actual display surface), the measured target positions 50 (symbols "θ") as well as the corresponding theoretical target positions 60 (symbols "+").

It is possible to choose for example the vertical direction of the axis 192 as favored direction of the dummy surface 111.

Then, for each pair formed of a measured target position 51 and of a theoretical target position 61 corresponding to the same target position 30 of the visual tracking protocol, a vertical disparity is calculated, denoted here Δv, corresponding to the distance, along the vertical direction, between the measured target position 51 and the theoretical target position 61 of said pair.

It is then possible to represent (see FIG. 14), for each target position 30 corresponding to one pair, all of the vertical disparities Δv in the frame of reference $R_{SCR}$ tied to the actual display surface 11. This set of all the vertical disparities is represented by the surface 100 in FIG. 11.

It would also be possible to choose a favored horizontal direction (along the axis 191 of FIG. 13) and calculate horizontal rather than vertical disparities.

Advantageously, a statistical processing of the calculated disparities is carried out to determine the visual behavior parameter.

This statistical processing may for example comprise the following operations:

produce one average <Δv> per display line, of the vertical disparities Δv. Measured curves 80, such as shown in FIGS. 15 and 16, in which the average <Δv> is dependent on the column index, are then obtained;

perform a linear regression so as to find an approximating straight line 81 which minimizes the disparity with the measured curves 80.

The slope of this approximating straight line 81 provides a parameter of the visual behavior of the individual 1 during the visual test protocol.

This slope is in particular defined so as to lie between 0 and 1. To do so, a minimum threshold value and a maximum threshold value are determined, making it possible to norm the coefficient, for ease of use. Thus the ratio (slope−minimum value/maximum value−minimum value) is calculated.

The maximum and minimum values may be obtained from a distribution of pre-recorded slopes or obtained from a plurality of individuals.

Specifically, when this slope is low (case of FIG. 12 with a slope of 0.17), this means that the average of the disparities between the measured target positions 50 and the theoretical target positions 60 is small. This corresponds to the visual behavior of an individual 1 who moves his eyes 3 a lot during the visual test.

In contrast, when this slope is high (case of FIG. 13 with a slope of 0.83), this means that the average of the disparities between the measured target positions 50 and the theoretical target positions 60 is large. This corresponds to the visual behavior of an individual 1 who moves his eyes 3 little during the visual test.

The invention claimed is:

1. A method for measuring the refraction of an individual by means of a refraction-measuring apparatus, comprising:
    a) an initial step of determining, with or without initial vision-correcting equipment, at least one initial value of a visuo-postural parameter of said individual;
    b) a step of processing said initial value of the visuo-postural parameter determined in step a) in order to deduce at least one initial value of an adjustment parameter of said refraction-measuring apparatus, said adjustment parameter being associated with said visuo-postural parameter;
    c) a step of adjusting said refraction-measuring apparatus depending on said initial value deduced in step b);
    d) a step of measuring the refraction of the individual by means of said refraction-measuring apparatus adjusted in step c);
    e) a step of equipping the individual with an item of vision-correcting test equipment suitable for correcting the refraction measured in step d);
    f) an additional step of determining, with said test equipment, at least one additional value of said visuo-postural parameter of said individual;
    g) an additional step of processing said additional value of the visuo-postural parameter determined in step f) in order to deduce at least one following value of said adjustment parameter associated with said visuo-postural parameter;
    h) a step of comparing said initial and following values of said adjustment parameter, and wherein:
    when the comparison of step h) indicates that said initial and following values of said adjustment parameter differ by more than a predetermined difference threshold, steps c) and d) of the method are repeated with said following value of the adjustment parameter in order to measure a new value of the refraction of the individual by means of said refraction-measuring apparatus adjusted depending on this following value of the adjustment parameter and said new value of the refraction and the value of the refraction measured in step d) are recorded; and when the comparison of step h) indicates that said initial and additional values differ by less than said predetermined difference threshold, said additional value determined in step f) and said refraction measured in step d) are recorded.

2. The measuring method as claimed in claim 1, wherein said visuo-postural parameter of the individual determined in step a) comprises one of the following parameters:
a natural posture of the head of the individual;
a visual behavior parameter in natural posture;
an eye/head coefficient;
a reading distance in near vision;
an offset value of a point of fixation with respect to the median plane of the head of the individual;
an angle of lowering of the gaze;
a parameter of convergence of the two eyes in near vision;
a gaze direction.

3. The measuring method as claimed in claim 2, wherein:
in step a), said individual is equipped with a spectacle frame; and
in step c), said measuring apparatus is also adjusted depending on at least one of the following complementary adjustment parameters:
a lens-eye distance;
a pantoscopic angle of said frame;
a wrap parameter of said frame;
a parameter of centralness of the ophthalmic lenses in said spectacle frame.

4. The measuring method as claimed in claim 2, wherein, said visuo-postural parameter of the individual being identical to said adjustment parameter of the refraction-measuring apparatus adjusted in step c), said processing of step b) consists in making said initial value of the adjustment parameter equal to said initial value of the visuo-postural parameter.

5. The measuring method as claimed in claim 1, wherein:
in step a), said individual is equipped with a spectacle frame; and
in step c), said measuring apparatus is also adjusted depending on at least one of the following complementary adjustment parameters:
a lens-eye distance;
a pantoscopic angle of said frame;
a wrap parameter of said frame;
a parameter of centralness of the ophthalmic lenses in said spectacle frame.

6. The measuring method of claim 5, wherein the spectacle frame comprises ophthalmic lenses.

7. The measuring method as claimed in claim 1, wherein, said visuo-postural parameter of the individual being identical to said adjustment parameter of the refraction-measuring apparatus adjusted in step c), said processing of step b) consists in making said initial value of the adjustment parameter equal to said initial value of the visuo-postural parameter.

8. An optical design method for designing an ophthalmic lens intended for an individual, comprising the following steps:
i) determining a value of the refraction of the individual by virtue of the implementation of the measuring method as claimed in claim 1; and
ii) determining the optical profile of said ophthalmic lens depending on said measured refraction value.

9. An ophthalmic lens further improving the visual comfort of an individual, said ophthalmic lens having an optical profile determined in step ii) of the optical design method of claim 8.

10. A pair of spectacles comprising at least one ophthalmic lens as claimed in claim 9.

11. A system for implementing the method for measuring the refraction of an individual as claimed in claim 1, said system comprising:
a vision-testing device suitable for evaluating said visuo-postural parameter of the individual;
computing means suitable for deducing a value of an adjustment parameter from a value of the visuo-postural parameter of the individual evaluated by the vision-testing device; and
a refraction-measuring apparatus suitable for being adjusted depending on said adjustment-parameter value deduced by the computing means and for measuring the refraction of the individual.

12. A non-transitory computer-readable medium on which is stored a computer program comprising code instructions for implementing step b) of the method for measuring the refraction of an individual as claimed in claim 1, when said program is executed on a computing means suitable for deducing a value of an adjustment parameter from a value of the visuo-postural parameter of the individual evaluated by the vision-testing device.

* * * * *